United States Patent [19]

Yamaguchi et al.

[11] Patent Number: 4,491,734
[45] Date of Patent: Jan. 1, 1985

[54] X-RAY DETECTOR AND METHOD OF MAKING SAME

[75] Inventors: Keiki Yamaguchi; Kazuyuki Tomarikawa; Haruo Kurochi; Jiro Namikawa; Shigeru Matsumura; Ryo Takahashi; Shiro Mori, all of Tokyo, Japan

[73] Assignee: Yokogawa Hokushin Electric Corporation, Tokyo, Japan

[21] Appl. No.: 452,714

[22] Filed: Dec. 23, 1982

[30] Foreign Application Priority Data

Nov. 2, 1982 [JP] Japan .................. 57-193157

[51] Int. Cl.³ .................. G01T 1/185; H01J 47/02
[52] U.S. Cl. .................. 250/385; 250/374
[58] Field of Search .................. 250/385, 374; 378/19; 313/256, 257, 258

[56] References Cited

U.S. PATENT DOCUMENTS

| Re. 30,644 | 6/1981 | Whetten et al. | 378/19 |
|---|---|---|---|
| 4,055,767 | 10/1977 | Allemand | 250/385 |
| 4,217,498 | 8/1980 | Racz et al. | 250/385 |
| 4,253,024 | 2/1981 | Peschmann | 378/19 |
| 4,457,009 | 6/1984 | Botden | 378/19 |

FOREIGN PATENT DOCUMENTS

| 143688 | 11/1979 | Japan | 250/385 |
|---|---|---|---|
| 159167 | 12/1980 | Japan | 250/385 |

Primary Examiner—Janice A. Howell
Assistant Examiner—Constantine Hannaher
Attorney, Agent, or Firm—Moonray Kojima

[57] ABSTRACT

An X-ray detector, used in an X-ray computerized tomograph systems, and method of making the same. The X-ray detector has a casing filled with gas for detecting X-rays, and flat signal electrode plates and bias electrode plates are disposed alternately at regular intervals within the casing to form a number of spatially partitioned detection chambers. When X-rays enter the detection chambers after being transmitted through an object under examination, the X-ray energy is converted into electric current flowing across the electrodes of the signal electrode plates, whereby the transmitted X-ray can be detected by an output circuit.

Improvements are provided to enable the signal electrode plates and the bias electrode plates to be more densely packed into the casing, thereby to obtain higher resolution X-ray computerized tomograms. In one embodiment, the signal electrode plate comprises an electrically conductive plate or substrate, insulating layers on both sides of the substrate, and electrodes on the other sides of the insulating layers. In another embodiment, flat insulating plates are used to securely attach and suitably position alternately, the signal and bias plates. In a further embodiment, electrically conductive rubber cords are used to connect the respective signal and bias plates to a read out circuit. Cut-outs and insulating devices may be used on the signal and bias plates or in the flat plates, to suitably connect and prevent erroneous connection of the cord to other than the associated plates. In a further embodiment, the signal plates have protrusions and printed circuit boards are provided with suitable electrical circuit patterns for connecting the signal plates to the read-out circuit. In another embodiment, a jig comprising two oppositely disposed blocks having channels therein for holding the side edges of the bias and signal plates, is provided, with the blocks being electrically insulating and substantially X-ray transparent.

10 Claims, 18 Drawing Figures

X-RAY DETECTOR AND METHOD OF MAKING SAME

BACKGROUND OF THE INVENTION

1. Field of Invention

This invention relates to an X-ray detector and method of making same; and, more particularly, to an X-ray detector for use in an X-ray computerized tomograph system, often referred to as "X-ray CT".

2. Description of the Prior Art

X-ray computerized tomograph systems generally have an X-ray tube for irradiating X-rays toward an object under examination and an X-ray detector consisting of a plurality of partitioned detection chambers for detecting X-rays transmitted through the object. The detected data are processed by a computer to obtain tomograms of the object.

Figure 1:
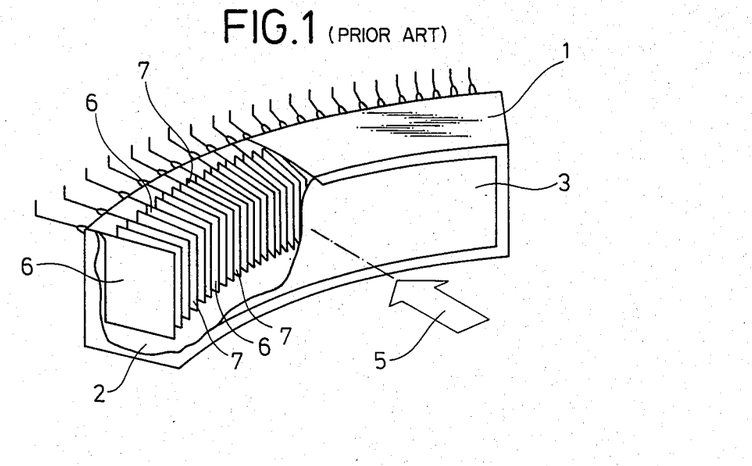
FIG. 1 is a schematic perspective view of a known X-ray detector with its casing partly cutaway to show its internal construction.

A conventional X-ray detector for use in X-ray CT systems is now described with reference to FIG. 1, to show the principles of operation thereof. FIG. 1 shows a conventional X-ray detector in schematic form with its casing partially cut away for sake of clarity. The detector has a casing 1 filled with a gas 2 under high pressure, for detecting X-rays. The kind of gas 2 is selected from known rare gases having large atomic numbers, such as, for example, xenon, krypton, argon, etc. The pressure and other factors, outside of the invention, as described herein, are determined in accordance with known techniques. The front portion 3 of casing 1 is made of a material which is substantially transparent to X-rays, such as plastics or aluminum. Gas 2 filling casing 1 is substantially opaque to radiations in the range of X-ray frequencies and front portion 3 is substantially transparent to such radiations. A beam of X-rays to be detected is indicated by arrow 5 and enters front portion 3 of casing 1, in the direction indicated by arrow 5, as shown in FIG. 1. Flat signal electrode plates 6 and flat bias electrode plates 7 are disposed alternately in substantially parallel relation to one another at substantially regular intervals, and are oriented substantially parallel to the incident direction of X-rays 5, as depicted. Thus, spaces formed by adjacent bias electrode plates and signal electrode plates define separate chambers for detecting the X-rays passing at different positions. Bias electrode plates 7 are connected to a bus line through which a DC voltage $V_1$ (see for example FIG. 6) is applied across signal electrode plates 6 and their respective neighboring electrode plates 7.

In the operation of the detector just described, when X-rays enter the different detection chambers, after penetrating the front portion 3, the X-rays interact with the atoms of gas 2, to produce electron-ion pairs, which flow along the electric field, thus to produce electric current across signal electrode plates 6 and their neighboring bias electrode plates 7. Since the value of the generated current corresponds to the incident X-ray energy, measurement of each current flowing into lead wires connected to the respective signal electrode plates 6, allows the determination of the X-ray energy for each respective detection chamber, which represents the different portions through which the X-rays passed through the object.

Advantageously, X-ray tomographs can produce sectional images, that would be obtained if the object undergoing medical examination were cut into slices, to assist the examination. Consequently, it is desired that the resultant sectional images provide a high resolution. That is, images distinctly depicting even minute portions within the human organs are desirable. The degree of such resolution is used as one of the major factors in judging the performance of X-ray tomograph systems.

The resolution of images depends strongly on the construction and characteristics of the X-ray detector used. Improvement in resolution can be achieved, it is believed, by more densely packing the signal and bias plates in the detector. Heretofore, various constraints have imposed limitations to high density packing of the electrode plates, as hereinafter discussed with reference to FIGS. 2-7.

Figure 2:
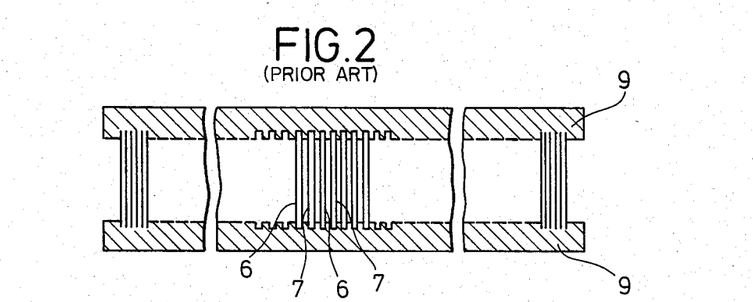
FIG. 2 is a fragmentary longitudinal cross section of the X-ray detector of FIG. 1, wherein signal plates and bias plates are disposed in a conventional manner.
Figure 3:
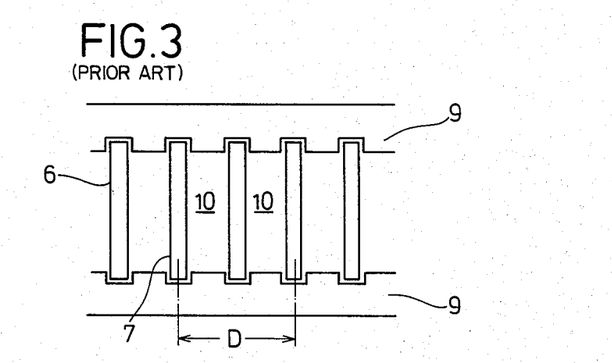
FIG. 3 is a fragmentary enlarged view of the X-ray detector of FIG. 1 illustrating the manner in which signal plates and bias plates are supported.

Referring to FIG. 2, there are shown signal electrode plates 6 and bias electrode plates 7. These plates are disposed alternately at substantially regular intervals in a conventional manner. This drawing figure is an elevational view taken in the incident direction of the X-rays shown in FIG. 1. Plates 6 and 7 are supported by supporting structure 9. FIG. 3 is a fragmentary enlarged view of the detector of FIGS. 1 and 2, and shows the manner in which plates 6 and 7 are supported by supporting structure 9. The structures 9 are provided with horizontally disposed grooves into which plates 6 and 7 are inserted at their upper and lower edges, and securely fixed to the supporting structure 9, with, for example, adhesive.

Since the signal and bias electrode plates 6 and 7 are required to be insulated from each other, the supporting structure 9 is usually made of an insulating material, such as ceramic. However, such material tends to crack easily, and hence, is not well suited for fine machining. Accordingly, as the intervals of the grooves formed in supporting structure 9 are made closer, the structure tends to crack more easily. Thus, a certain practical limit is imposed on the closeness of the grooves, and hence the resolution of the tomograms. This practical limit for prior arrangement leaves much to be desired in terms of resolution of the obtained tomograms.

Figure 4:
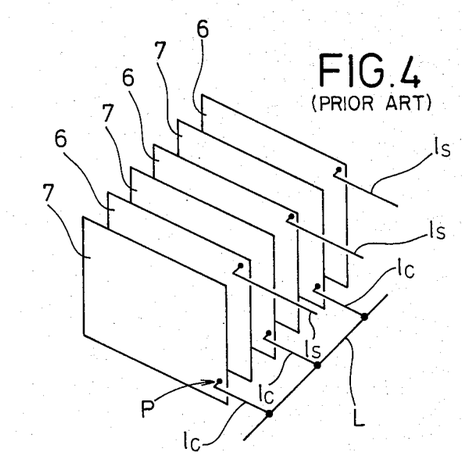
FIG. 4 is a perspective view of signal electrode plates, bias electrode plates and associated conventional connecting devices therefor.

Moreover, the prior art is further deficient in that signal electrode plates 6 are required to have lead wires attached thereto, in order to obtain electric currents proportional to the respective X-ray energies incident on the respective detection chambers. Also, bias electrode plates 7 are required to be connected to a high voltage power source, for example, of about 500 volts. For these purposes, the prior art has used a connecting structure, such as shown in FIG. 4, wherein lead wires $l_s$ and $l_c$ and bus line L, which is maintained at a high voltage, are shown. Lead wires $l_s$ and $l_c$ are connected to electrode plates 6 and 7, respectively, by soldering, bonding or the like. Accordingly, connecting points P protrude perpendicularly from the sides of the plates, thus preventing close arrangement of the adjacent plates 6 and 7.

Figure 5:
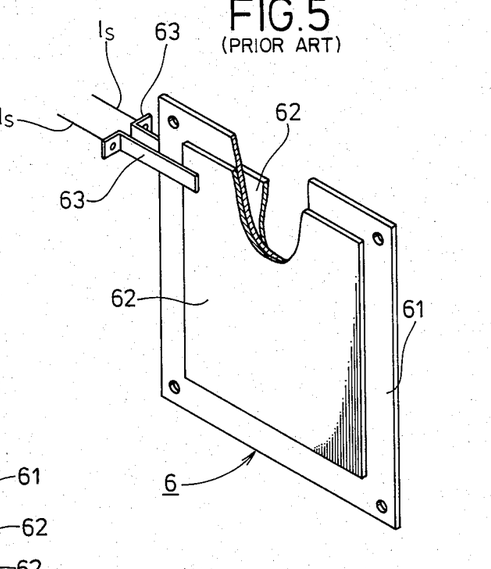
FIG. 5 is a perspective view of a known signal electrode plate.

Referring next to FIG. 5, a signal electrode plate 6, provided with conventional means for heightening the resolution of images, is shown. The plates 6 comprise a flat plate 61 made of an insulating material, and electrodes 62 on opposite sides of plate 61, and made of electrically conductive material. Electrodes 62 are electrically connected to their respective lead wires $l_s$ via metallic clips 63, as depicted.

Figure 6:
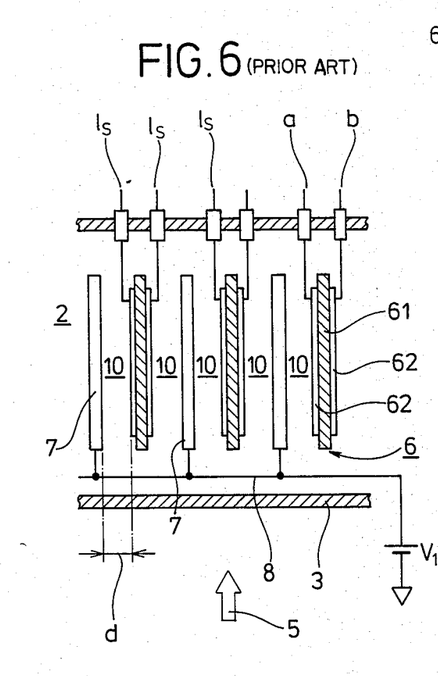
FIG. 6 shows an arrangement of signal and bias electrode plates using the signal plates of FIG. 5.

A conventional x-ray detector, using signal electrode plates 6, such as depicted in FIG. 5, has an electrode arrangement, such as shown in FIG. 6, wherein parts described already in connection with FIGS. 1-5, and denoted with like reference numerals, are not again described for sake of simplicity and clarity of description. In FIG. 6, using the plate arrangement of FIG. 5, one detection chamber 10, for one channel, has a width d. On the other hand, as shown in FIG. 3, if each signal electrode plate 6 is made simply of a metallic plate, such as in FIGS. 1,2,3,4, detection chambers corresponding to one channel, have width D. As can be seen from these two FIGS. 6 and 3, the relationship $d \approx D/2$ holds. Thus, the arrangement of FIG. 6 can be said to be an improvement in resolution, to the arrangement of FIG. 3. However, such improvement per se is still not sufficient. The X-ray detector of FIG. 6 still has a disadvantage which prevents the obtaining of good distinct and clear tomograms. This disadvantage will now be described.

Figures 7, 8, 9:
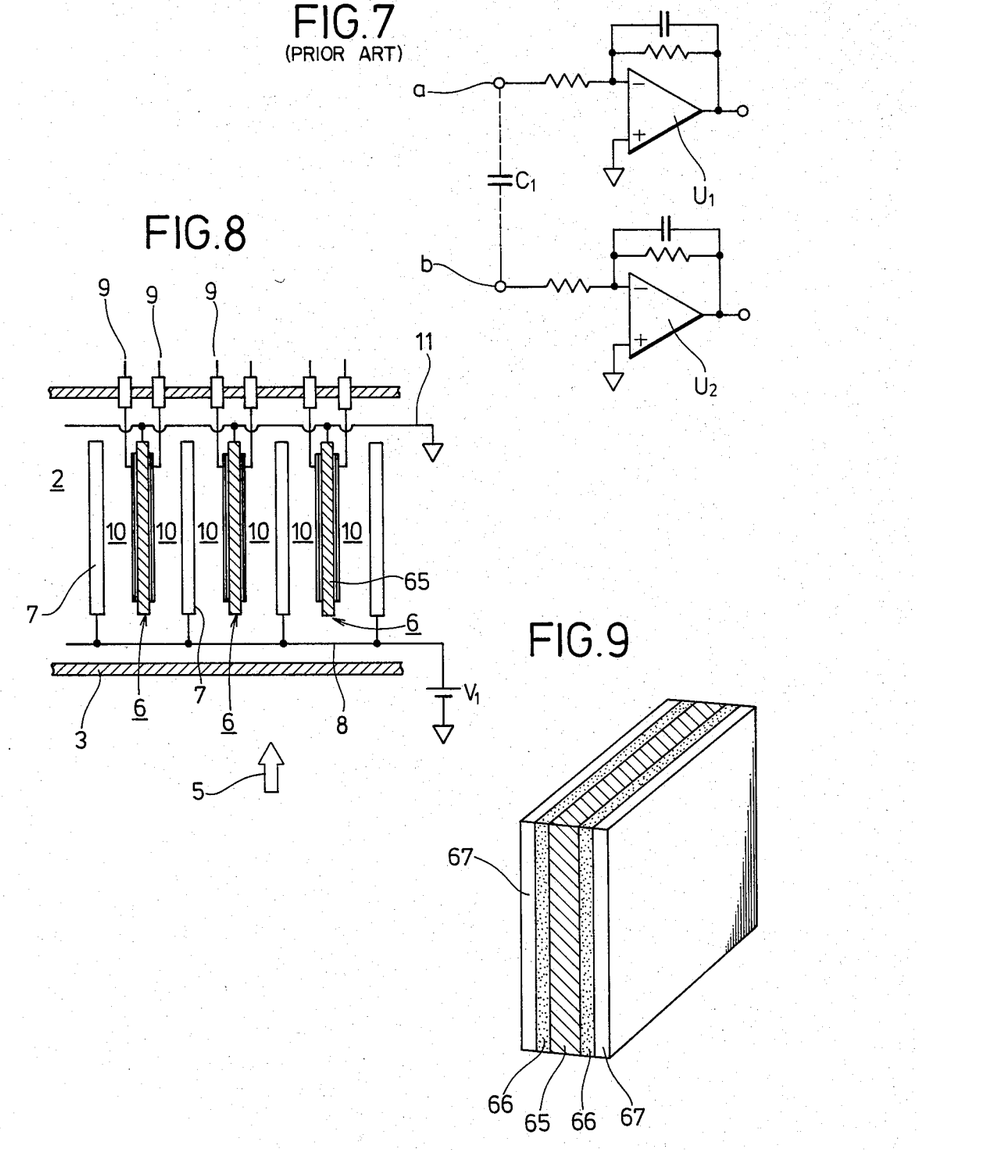
FIG. 7 is a diagram of an input circuit used with the signal electrode plate of FIG. 6.
FIG. 8 depicts an illustrative embodiment of the invention.
FIG. 9 is a perspective view of an illustrative signal electrode plate used in the invention.

Referring again to FIG. 6, a large capacitance $C_1$ (see FIG. 7) is produced between each adjacent channel, for example, a and b, because of the interposing of insulator 61. Electric current produced across two channels is applied to an output circuit, such as shown in FIG. 7, wherein current is converted into voltage by way of an integrator circuit (not shown) to measure the value of the current. The circuit of FIG. 7 includes amplifiers $U_1$ and $U_2$. The aforementioned capacitance $C_1$ causes interference between the two channels, thus, hindering production of distinct and clear tomograms of the different channels.

Thus, the prior art X-ray computerized tomograph systems are lacking in X-ray detectors, which can produce high resolution tomographs, consistent with acceptable costs and operating characteristics.

SUMMARY OF THE INVENTION

Accordingly, an object of the invention is to eliminate and overcome the aforementioned and other deficiencies and disadvantages of the prior art.

Another object is to provide an improved X-ray detector and method of making same, wherein the density of detection chambers is optimal and high resolution X-ray tomograms are obtained.

A further object is to provide a signal electrode and process of making same, wherein, the signal electrode construction facilitates placement thereof vis-a-vis an adjacent bias electrode.

A still further object is to improve X-ray detector components and connector elements whereby easier and denser packing of the components is made possible.

Another object is to provide components and method of making same, for positioning the signal and bias electrodes in denser packing relations and thereby obtain higher resolution.

The foregoing and other objects are attained in an illustrative embodiment of the invention which encompasses apparatus and method of making same, and comprises a signal plate comprising an electrically conductive plate or substrate, an insulating layer on opposite sides of the substrate, and electrically conductive electrodes on the other sides of the insulating layers. A pair of flat electrically insulating plates are securely attached, such as by use of adhesives, to the upper and lower edges of the signal plates and bias plates with the signal and bias plates being alternately disposed thereby to form a plurality of detecting chambers therebetween. A pair of electrically conductive rubber cords is provided on respective insulating plates for connecting to the respective signal and bias plates for selective readout of signals from each chamber. By suitable cutouts or use of insulating devices, the signal plates and bias plates will be electrically insulated from the cord connected to the other plates. Electrical connection of the signal plates is accomplished using protrusions located at the side edges of the signal plates and connecting the protrusions with printed circuit patterns. The alternately disposed signal and bias plates may be disposed to be held by a pair of oppositely disposed blocks having channels therein into which the signal and bias plates are held, with the blocks being electrically insulating and X-ray transparent. Advantageously, the resulting X-ray detector has highly dense array of detecting chambers and produces high resolution X-ray computerized tomograms.

A feature of the invention is a signal electrode used in an X-ray detector for X-ray computerized tomograph apparatus or system, having an electrically conductive plate or substrate, an insulating layer on both sides of the substrate, and electrically conductive electrodes on the other sides of the insulating layers.

A further feature is a pair of electrically insulating plates securely attached, such as by use of adhesives, to the upper and lower edges of the plurality of signal electrodes and bias electrodes with the signal electrodes being arranged alternately with the bias electrodes thereby forming a plurality of detecting chambers.

Another feature is the use of a pair of electrically conductive rubber cords disposed on the electrically insulating plates which are attached to signal electrodes and bias electrodes; and the electrical connection of one cord to the signal electrodes and the other cord to the bias electrodes.

A further feature is the use of cut-outs in the signal electrodes and bias electrodes to prevent erroneous electrical contact with the cord connected to the opposite electrode.

Another feature is the use of insulating material to prevent erroneous contact of the signal and bias electrodes onto the cords connected to the other electrodes.

A still further feature is the use of a protrusion on the signal electrodes for connecting to the outside readout circuit, and the use of printed circuits having suitable circuit patterns for connecting to either the substrate, or the two outside electrodes of the signal plate.

Another feature is the use of a jig comprising two electrically insulating and X-ray transparent blocks having a plurality of channels into which the side edges of the signal and bias electrodes are held.

Other features are methods of producing the above features.

DESCRIPTION OF PREFERRED EMBODIMENTS

Referring to FIGS. 8 and 9, there are shown the construction and arrangement of signal electrode plates used for an X-ray detector according to the invention, together with the electrical connections therefor. These figures and the remaining figures are understood to be described with reference to the operating principles set forth above in FIGS. 1-6. Where common elements and operating principles are involved, no further descriptions will be given. The remaining components of an X-ray computerized tomograph system wherein the invention may be used, are known and can be found in any suitable commercially available handbook. Accordingly, they are not further described. The X-ray detector described herein can be readily employed in known X-ray computerized tomograph systems.

Turning to FIG. 8, there is depicted an arrangement of electrode plates of an X-ray detector and electrical connecting devices therefor. In FIG. 9, the signal electrode plate comprises a substrate or flat guard plate 65 made of electrically conductive material, and insulating layers 66 formed on opposite surfaces of the plate 65. Formed on the opposite sides of the insulating layers 66 are electrodes 67 made of electrically conductive material. These materials may be coated or formed, such as by etching, on each other in known manners. When X-rays enter a detection chamber formed of a pair of signal and bias electrode plates, secondary photons will be produced thereby. In order to prevent such photons from intruding into neighboring, i.e. next adjacent, chambers, at least one of the plates or substrates 65 (see FIG. 9) and electrodes 67 is preferably made of a material which is substantially opaque to X-rays. It is known that molybdenum, tantalum, tungsten, etc, are electrically conductive and also substantially opaque to X-rays, and hence should so be used.

As a specific example, guard plate or substrate 65 is made of tungsten or molybdenum, and flexible printed boards are attached to opposite surfaces of the plate 65 with appropriate means such as by electro-deposition. In one example, each printed board was made by depositing copper onto one insulating layer 66, which was made of a polyimide, in vacuum to form electrode 67 on the insulating layer 66.

Referring to FIG. 8 which is a plan view, the X-ray detector incorporates signal electrode plates 6 constructed as shown in FIG. 9 and guard plates 65 of plates 6 are grounded via lead 11. Lead wires 9 are connected to their respective electrodes 67 to obtain ionization current. Plates 7 are connected to power source $V_1$. Thus, in the novel illustrative embodiment of the invention, since guard plates 65 are grounded, the aforementioned capacitance $C_1$ (see FIG. 7 and description thereof) will not be developed across adjacent channels. The other components having like reference numerals are similar to those previously shown and hence are not again described. The same will apply for the other drawing figures.

Figure 10:
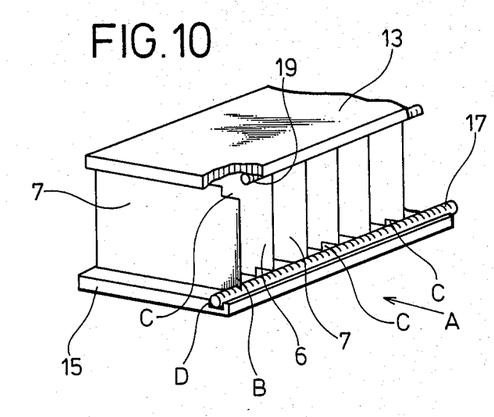
FIGS. 10-13 depict other illustrative embodiments of the invention.
Figure 11:
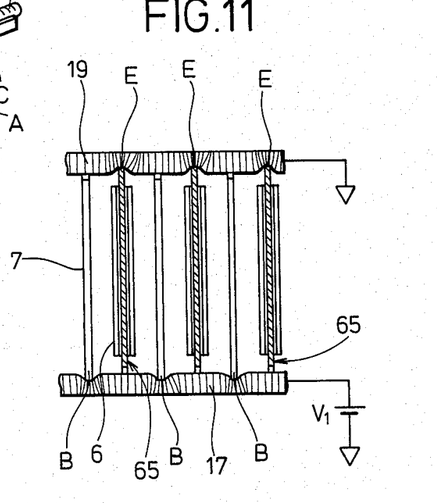

Referring now to FIGS. 10 and 11, there are shown principal portions of another X-ray detector of the invention, to illustrate electrical connecting devices associated with electrode plates 7 and guard plates 65 of the signal plates 6. FIG. 10 is a perspective view of the detector, while FIG. 11 is an elevational view, in section, of the detector of FIG. 10, as viewed from the direction indicated by arrow A (in FIG. 1). In these figures, signal electrode plates 6 and bias electrode plates 7, are similar to those indicated by like reference numerals in the previous figures, except that each plate is provided with a recess portion C. Electrically conductive plates 6 and 7 are supported by flat insulating plates 13 and 15 in a manner described later. Plates 13 and 15 are each provided with a concave cut out portion, as indicated by D in FIG. 10. Cords 17 and 19, both of which are made of electrically conductive rubber, are disposed in the concave portions D in plates 15 and 13, respectively. A voltage $V_1$ (See FIG. 11) is applied to cord 17, while cord 19 is grounded.

In the detector, constructed in the manner as described hereinabove, bias electrode plates 7 are pressed into cut out or recessed portions of cord 17 at positions B. Similarly, guard plates 65 (see FIG. 11) of signal plates 6 are pressed into cut out or recessed portions of cord 19 at positions E. Accordingly, plates 7 and 65 are electrically connected to electrically conductive cords 17 and 19, respectively, but do not touch the other cords, 19 and 17, respectively, due to the recesses C formed in plates 6 and 7. In this way, only if plates 7 and 65 are disposed in position, the wiring operation of the lead wires $l_c$ is not required. Thus, no perpendicularly extended lead terminals, need exist, which differs in an advantageous manner from the extended terminals described with reference to the prior art in FIG. 4. As a result, plates 6 and 7 can be positioned closer to each other than would otherwise be possible.

Although plate 65 has been described as being used as the signal plate 6, with appropriate connections, electrodes 67 (see FIG. 9) on opposite sides of plate 65 and coating insulating layer 66, can be used with a respective oppositely disposed bias plate 7. In this manner, each detecting chamber will always have a separate signal electrode 67.

Figure 12:
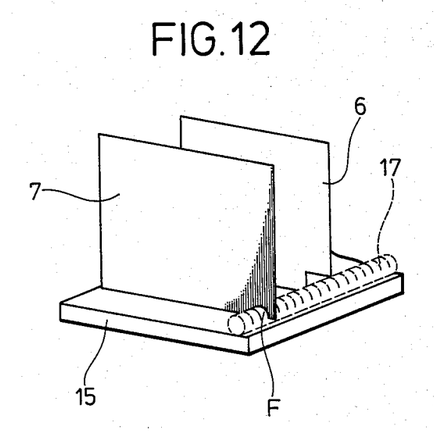

Although rubber cords 17 and 19 are positioned between plates 13 and 15 (see FIG. 10) in geometrical relationship as depicted, with guard plates 65 and electrodes 7, the instant invention is not limited to this arrangement. Rather, rubber cords 17 and 19 may be disposed in any arbitrary relationship with electrode plates 6 and 7. Furthermore, concave portions D formed, respectively, in plates 13 and 15, for positioning cords 17 and 19, are not essential to the present invention. For example, as depicted in FIG. 12, electrode plates 6 and 7, may be each formed with a recess F of an appropriate size and shape, and concave portion D will not be necessary.

Figure 13:
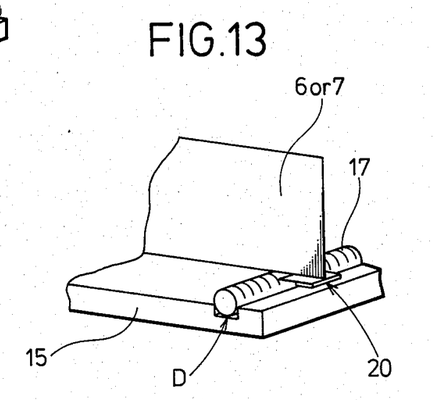

In addition, in the embodiment depicted in FIGS. 10 and 11, electrode plates 6 and 7 are each provided with a hollow cut-out portion C in order to prevent them from contacting the wrong rubber cords, and thus prevent erroneous electrical connections. However, the hollowed out portions are not essential to the invention. For instance, in the embodiment depicted in FIG. 13, cord 17 is partially embedded in concave portion D formed in flat plate 15, and insulators 20 are installed among electrodes 6 and 7 and cords 17 and 19, thus dispensing with hollowed out portions C. Also, in the above embodiments, electrically conductive rubber is shaped into a cord configuration, but, it can also be formed into other shapes, such as belt, rope, plate, rod, etc.

Figures 14, 15, 16:
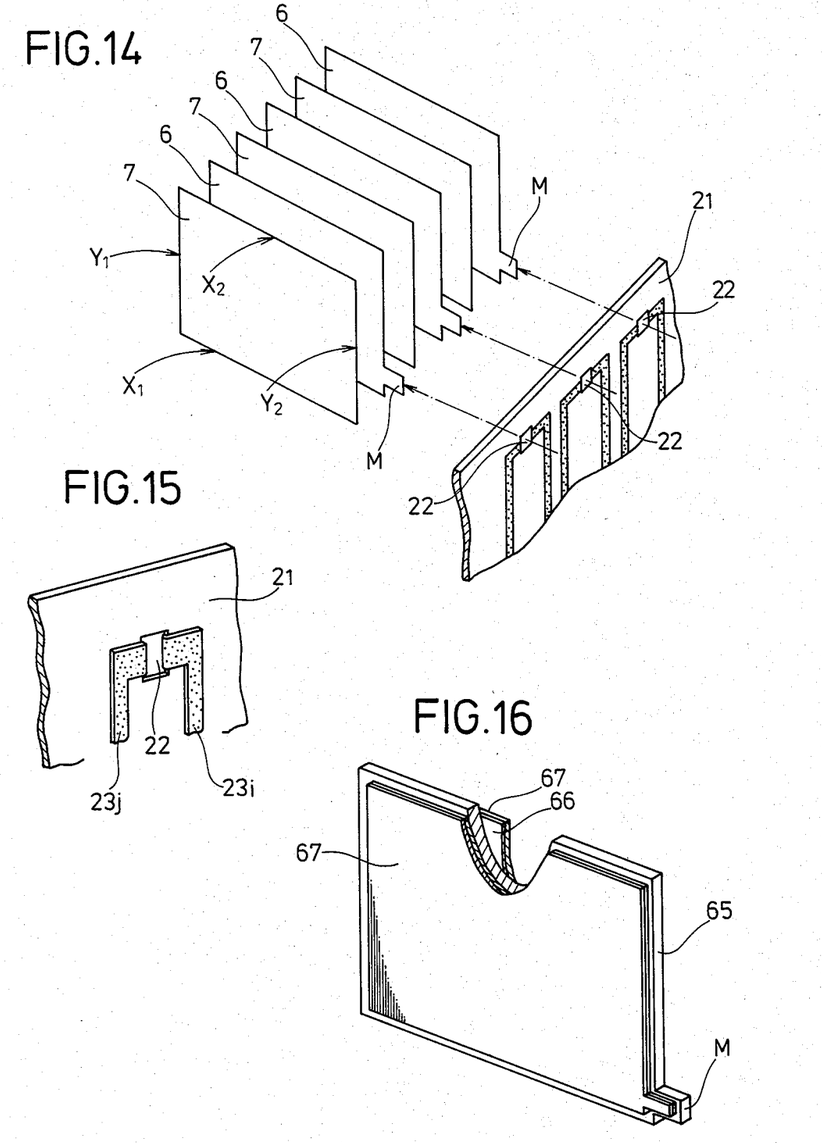
FIGS. 14-16 depict still further illustrative embodiments of the invention, and using a printed board as electrical connection devices.

Referring to FIGS. 14–16, there is depicted the principal portion of another embodiment of an X-ray detector according to the present invention. The detector includes means electrically connected to electrodes 67 (see FIG. 16) of the signal electrode plates 6 for deriving ionization current. More specifically, signal electrode plates 6 and bias electrode plates 7 are similar to those as described above except that each plate 6 has a protrusion M as depicted in FIGS. 14 and 16. A printed circuit board 21 is provided with holes 22 into which protrusions M of plates 6 are inserted in alignment therewith. Electrically conductive patterns $23_i$ and $23_j$ (see FIG. 15) are provided at least in a portion of each hole 22. FIG. 15 is an enlarged view of one hole 22 and the associated conductive patterns $23_i$ and $23_j$. Of course, patterns $23_i$ and $23_j$ are circuits which are electrically isolated from each other. After protrusions M are fitted into holes 22, as depicted in FIG. 14, electrodes 6 on the front side and electrodes 7 on the rear side are electrically connected and fastened to conductive patterns $23_i$ and $23_j$, respectively, by soldering or with electrically conductive adhesive or other means, it being understood that the present invention is not limited to these specific electrical connecting means.

Referring again to FIGS. 14–16, each protrusion M of plates 6 is formed into a rectangular shape, but the invention is not limited to this shape. For example, it may be formed so as to have a rounded tip or formed into a tapered shape for easy insertion into holes 22. Also, the shape of holes 22 formed in board 21 is not limited to that shown in FIGS. 14 and 15. The aforementioned printed circuit board 21 is usually a flexible board, but is not limited thereto, and can be even a rigid printed board. Furthermore, each protrusion M of plates 6 may be formed on any one of the four sides (FIG. 14) $X_1$, $X_2$, $Y_1$ and $Y_2$ of the plates.

In FIG. 16, plate 6 is depicted having a cut out portion, to facilitate understanding of the construction of the plate 6. In actuality, plate 6 is not provided with the hollowed out portion, as depicted in FIG. 16.

Thus, advantageously, the embodiment shown in FIGS. 14–16 does not require that lead wires $l_s$ be connected to electrodes 67 by way of perpendicularly extended terminals, on both sides of plates 6 as was the case, for example, in the prior art. As depicted, electrode 67 on the left, will contact conductive pattern $23_j$; and electrode 67 on the right will contact conductive pattern $23_i$ (see FIGS. 15 and 16 together). In this manner, one plate 6 will have a separate electrode 67 associated with adjacent plate 7 on either side thus forming adjacent detecting chambers having separate signal plates. On the other hand, as in the other embodiments, substrate 65 may be used, and adjacent detecting chambers will have common signal electrodes. Either can be used. The result is that electrode plates 6 and 7 can be disposed closer together than would be the case with the prior art arrangements.

Figure 17:
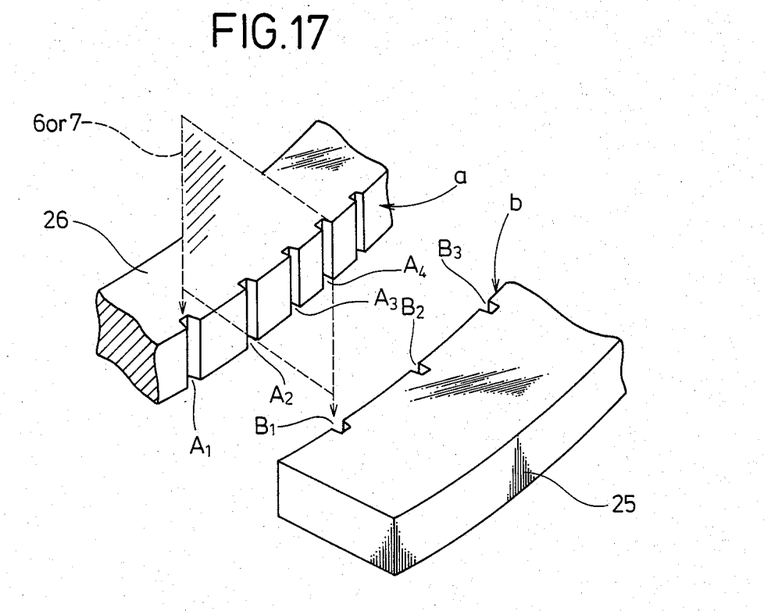
FIGS. 17-18, are fragmentary perspective views of another illustrative embodiment of the invention and using a jig structure for placement of the electrode plates.
Figure 18:
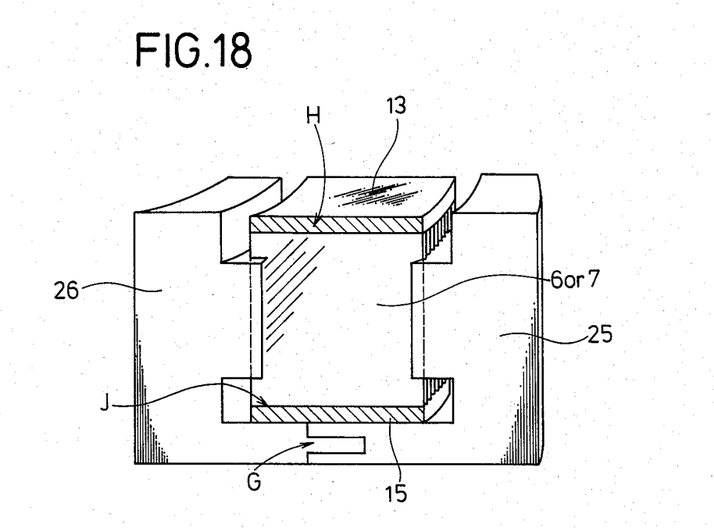

Referring to FIGS. 17 and 18, there is depicted principal portions of a still further embodiment. This detector uses flat plates having no horizontally disposed grooves, in contrast, for example, to the prior arrangement of FIGS. 2 and 3, wherein the detector structure 9 had grooves to hold the upper and lower edges of the plates 6 and 7. Briefly, this illustrative detector has a casing filled with gas for detecting X-rays. In this casing, a pair of flat plates (13 and 15 in FIG. 18) are positioned opposite to each other, and signal electrode plates 6 and bias electrode plates 7, are disposed alternately at substantially regular intervals in face-to-face relation, in the space between the flat plates (13 and 15 in FIG. 18). The flat plates 13 and 15 are of electrically insulating material. The upper and lower edges of each electrode plate 6 or 7 are securely attached to the oppositely disposed flat plates (13 and 15) with adhesive. Each of the flat plates does not have any horizontal grooves for holding the upper and lower edges of the plates 6 and 7, as in the prior arrangements (see, for example, FIG. 3). This arrangement is thus similar to that shown in FIG. 10, but differs in ways to be described hereinafter.

FIG. 17 shows the manner in which signal electrode plates 6 and bias electrode plates 7 are arranged using a jig. FIG. 18 depicts such a jig holding side edges of plates 6 and 7, and flat plates 13 and 15 holding the upper and lower edges of plates 6 and 7. Jig 17 comprises a pair of blocks 25 and 26. Although both blocks can be substantially transparent to X-rays, at least the block through which the X-rays must pass to interact in the detecting chambers, must be substantially transparent to X-rays. Also, the blocks 25 and 26, are of electrically insulating material. Block 25 has a curved surface b provided with a plurality of vertically extending grooves $A_1$, $A_2$, $A_3$, etc; as depicted in FIG. 17. Similarly, block 26 has a curved surface a, which is parallel to surface b and is provided with a plurality of vertically extending grooves $B_1$, $B_2$, $B_3$, etc. Grooves $A_1$ and $B_1$; $A_2$ and $B_2$, etc., are disposed opposite to each other and form associated pairs, for holding the side edges of electrode plates 6 or 7. Electrode plates 6 and 7, are alternately inserted in the the grooves, as depicted in FIGS. 17 and 18. Thus, by inserting the plates 6 and 7 alternately into the successive pairs of grooves, an arrangement is obtained wherein the plates 6 and 7 are disposed in face to face relations, and at substantially regular intervals and positioned substantially parallel to the direction of travel of the X-rays 5 (see FIG. 8), with a plurality of detection chambers thus formed thereby.

Referring particularly to FIG. 18, two blocks 25 and 26 constituting the jig can be separated from each other at position G. The jig may comprise either a one block or two block or more, arrangement. Furthermore, the blocks may be joined together and separated from each other in any arbitrary manner as desired. Also depicted are flat plates 13 and 15, of electrically insulating material, which are advantageously employed in the invention. Differing from the known guide device 9 (such as depicted in FIG. 3) plates 13 and 15 do not have grooves for holding the plates 6 and 7. Plates 13 and 15 may be made, for example, of almilite, which is prepared from aluminum by anodic oxidation.

An example of a method of making X-ray detectors according to the invention will now be described with reference to FIG. 18. First, blocks 25 and 26 of the jig, are joined together at position G and then the flat plate 15 is positioned on the underside of the jig in the manner depicted. Thereafter, the plates 6 and 7 are inserted into the respective pairs of grooves (e.g. $A_1B_1$ ... in FIG. 17) formed in the jig as above described and having the lower edges touching plate 15; and then, plate 13 is place on the upper edges of plates 6 and 7. Under this condition, the upper and lower edges of plates 6 and 7 are then securely attached to surfaces H and J of plates 13 and 15, with, for example, adhesive, which may be applied to the surfaces of plates 13 and 15 and/or the upper and lower edges of plates 6 and 7, prior to such assembly. Alternately, after the components are arranged as depicted in FIG. 18, adhesive may be applied to the appropriate parts for adhesion. It is also possible to align plates 6 and 7 with the respective pair of grooves (e.g $A_1B_1$ ... etc) using the jig, and then to dispose plates 13 and 15 such that they contact the upper and lower edges of plates 6 and 7, when construction of the jig allows for such arrangement.

In this manner, the X-ray detector depicted in FIGS. 17 and 18 dispenses with conventional guide means, which are usually provided with grooves, such as depicted in FIG. 3. Instead, the novel detector of the invention uses simple, flat plates which do not crack easily because of the absence of grooves, and plates 6 and 7 can be positioned closer to each other than would be possible with the prior art. As a result, advantageously, higher resolutions are possible.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. In an X-ray detector comprising
   casing means;
   gas filled in said casing means for detecting X-rays;
   a plurality of signal electrodes;
   a plurality of bias electrodes;
   means for positioning said signal electrodes and said bias electrodes within said casing means to form a plurality of detection chambers between each adjacent signal electrode and bias electrode; and
   means for selectively reading signals produced by said X-rays in each said chamber;
   the improvement comprising
   each of said signal electrodes comprises a flat electrically conductive substrate having two sides, insulating layers formed on said two sides of said substrate, and a pair of electrically conductive electrodes formed on said insulating layers; and
   said means for positioning comprises a pair of flat electrically insulating plates for securely holding said signal electrode and said bias electrodes, whereby said signal electrodes and said bias electrodes are positioned alternately with their sides in face to face configuration.

2. The detector of claim 1, wherein said means for selectively reading signals comprises a first electrically conductive rubber cord, and a second electrically conductive rubber cord; and wherein said bias electrodes are electrically connected to said first cord, and said substrates of said signal electrodes are electrically connected to said second cord.

3. The detector of claim 1, wherein said signal electrodes comprise a protrusion, and wherein said means for selectively reading comprises a printed circuit board having holes therein, into which said protrusions of said signal electrodes are inserted, said printed circuit board having a pair of electrically conductive circuit patterns for each hole, said pair of patterns occupying at least a portion of each hole; and wherein said electrically conductive electrodes disposed on opposite sides of each signal electrode are each electrically connected to respective ones of said circuit patterns at each hole.

4. The detector of claim 2, wherein said flat insulating plates have cut out portions, into which said cords are disposed.

5. The detector of claim 2, wherein said signal electrodes have cut out portions at positions whereby said first cord avoids electrical contact to said signal electrodes; and wherein said bias electrode has cut out portions at positions whereby said second cord avoids electrical contact to said bias electrodes.

6. The detector of claim 2, wherein said insulating means are provided to prevent electrical contact between said signal electrode and said first cord, and between said bias electrode and said second cord.

7. The detector of claim 2, wherein said means for positioning said signal electrodes and said bias electrodes, comprises a pair of blocks having a plurality of channels therein for placement of said signal electrodes and said bias electrodes, said blocks being disposed to be substantially perpendicular to the direction of travel of said X-rays, with said signal and said bias electrodes being substantially parallel to said direction of travel of said X-rays, and said blocks being of a material which is substantially transparent to said X-rays, and electrically insulating.

8. The detector of claim 1, wherein said flat plates are attached to said signal electrodes and said bias electrodes by adhesive.

9. A method of making an X-ray detector comprising
   casing means;
   gas filled inside said casing means for detecting X-rays;
   a plurality of signal electrodes;
   a plurality of bias electrodes;
   means for positioning said signal electrodes and said bias electrodes within said casing means to form a plurality of detection chambers between each adjacent signal electrode and bias electrode; and
   means for selectively reading signals produced by said X-rays in each said chamber;
   said method comprising the steps of
   preparing a jig having two curved surfaces, said curved surfaces being substantially parallel to each other and provided with a plurality of pairs of opposed grooves for holding side edges of said signal electrodes and said bias electrodes;
   inserting said side edges of said signal and bias electrodes into said grooves of said jig to arrange said signal electrodes to be face to face with said bias electrodes;
   arranging flat plates on the upper and lower edges of said signal electrodes and said bias electrodes; and
   attaching said flat plates to said upper and lower edges of said signal electrodes and said bias electrodes.

10. The method of claim 9, wherein said flat plates are attached to said signal and bias electrodes by adhesive.

* * * * *